(12) United States Patent
Taylor et al.

(10) Patent No.: US 7,288,513 B2
(45) Date of Patent: Oct. 30, 2007

(54) DISINFECTING AND SANITIZING ARTICLE FOR HANDS AND SKIN AND HARD SURFACES

(75) Inventors: Paul M. Taylor, Overland Park, MO (US); Peter E. Keilman, Kansas City, MO (US); Khue Vue, Olathe, KS (US); Christopher J. Plotz, Olathe, KS (US)

(73) Assignee: Illinois Tool Works, Inc., Glenview, IL (US)

( * ) Notice: Subject to any disclaimer, the term of this patent is extended or adjusted under 35 U.S.C. 154(b) by 0 days.

(21) Appl. No.: 11/105,784

(22) Filed: Apr. 14, 2005

(65) Prior Publication Data

US 2006/0234894 A1    Oct. 19, 2006

(51) Int. Cl.
C11D 1/825 (2006.01)
C11D 3/48 (2006.01)
C11D 3/43 (2006.01)

(52) U.S. Cl. ............... 510/439; 510/130; 510/295; 510/356; 510/421; 510/432; 510/463; 510/438; 510/382; 510/384; 510/386

(58) Field of Classification Search ............... 510/130, 510/295, 356, 421, 432, 463, 438, 439, 382, 510/384, 386
See application file for complete search history.

(56) References Cited

U.S. PATENT DOCUMENTS

| | | | |
|---|---|---|---|
| 3,396,419 A | 8/1968 | Richter | |
| 4,833,003 A | 5/1989 | Win et al. | |
| 4,847,089 A | 7/1989 | Kramer et al. | |
| 4,965,063 A * | 10/1990 | Casey et al. ............... | 510/100 |
| 5,141,803 A | 8/1992 | Pregozen et al. | |
| 5,439,609 A | 8/1995 | Paszek | |
| 5,460,742 A * | 10/1995 | Cavanagh et al. ........ | 510/398 |
| 5,522,942 A | 6/1996 | Graubart et al. | |
| 5,651,974 A * | 7/1997 | Asaka .................... | 424/405 |
| 5,698,475 A | 12/1997 | Vlasblom | |
| 5,891,392 A | 4/1999 | Monticello et al. | |
| 5,929,016 A | 7/1999 | Harrison | |
| 5,962,001 A * | 10/1999 | Rose et al. ................ | 424/404 |
| 6,017,869 A | 1/2000 | Lu et al. | |
| 6,022,841 A | 2/2000 | Lu et al. | |
| 6,075,002 A | 6/2000 | Cheung et al. | |
| 6,090,771 A | 7/2000 | Burt et al. | |
| 6,106,774 A | 8/2000 | Monticello et al. | |
| 6,136,770 A | 10/2000 | Cheung et al. | |
| 6,143,710 A | 11/2000 | Lu et al. | |
| 6,146,651 A * | 11/2000 | Kritzler .................... | 424/404 |
| 6,184,195 B1 * | 2/2001 | Cheung et al. ............ | 510/432 |
| 6,221,823 B1 | 4/2001 | Crisanti et al. | |
| 6,239,092 B1 | 5/2001 | Papasso et al. | |
| 6,268,327 B1 | 7/2001 | Lu et al. | |
| 6,306,810 B1 | 10/2001 | Cheung et al. | |
| 6,358,900 B1 | 3/2002 | Wigley et al. | |
| 6,375,964 B1 | 4/2002 | Cornelius | |
| 6,376,448 B1 | 4/2002 | Colurciello, Jr. et al. | |
| 6,440,916 B1 | 8/2002 | Cheung et al. | |
| 6,503,952 B2 * | 1/2003 | Modak et al. ............. | 514/635 |
| 6,514,923 B1 | 2/2003 | Cheung et al. | |
| 6,559,111 B2 | 5/2003 | Colurciello, Jr. et al. | |
| 6,667,289 B2 | 12/2003 | Harrison et al. | |
| 6,734,157 B2 | 5/2004 | Radwanski et al. | |
| 6,753,063 B1 * | 6/2004 | Pung et al. ................ | 428/152 |
| 6,841,528 B2 | 1/2005 | Kaiser et al. | |

OTHER PUBLICATIONS

European Search Report dated Aug. 2, 2006.

* cited by examiner

*Primary Examiner*—Charles Boyer
(74) *Attorney, Agent, or Firm*—Mark W. Croll; Donald J. Breh; Levenfeld Pearlstein, LLC

(57) ABSTRACT

A disinfecting and sanitizing article is adapted for use on objects to be disinfected and sanitized, including skin and hands and nonporous hard surfaces. The article is formed from a porous substrate formed from an absorbent fibrous matrix. A disinfecting and sanitizing agent is formed as a liquid composition that is absorbed into the substrate. The composition is formulated from an organic solvent present in a concentration of about 10 percent to 40 percent by weight, a surfactant present in a concentration of about 0.5 percent to 20 percent by weight, one or more pathogen killing agents present in a concentration of about 0.255 percent to 10.5 percent by weight, an emollient present in a concentration of about 0.05 percent to 3.0 percent by weight, and water present in a concentration of about 50.0 percent to 89.9 percent by weight. Application of the article provides an abrasive disinfecting and sanitizing action by a scrubbing action on the surface of the object to disinfected and sanitized.

5 Claims, 1 Drawing Sheet

DISINFECTING AND SANITIZING ARTICLE FOR HANDS AND SKIN AND HARD SURFACES

BACKGROUND OF THE INVENTION

The present invention pertains to cleaners and cleaning articles. More particularly, the present invention relates to a disinfecting and sanitizing article for use on skin and hands, as well as on hard surfaces.

Disinfectant and sanitizing compositions are generally formulated to kill specific and targeted pathogens. These compositions can contain a variety of germ-killing chemicals individually and in combination, with the specific intent of eradicating the targeted pathogen. These compositions can include phenols, quaternary ammonium chlorides, glutaraldehydes, iodines and alcohols. If cleaning properties are also desired the compositions can include surfactants (generally non-ionic surfactants) and water to dilute the germ-killing chemicals to a safe user level. Other additives may also be used, such as perfumes, dyes, wetting agents, phosphates, silicates and solvents, to accomplish specific results. These products are offered in ready-to-use concentrations as well as highly dilutable concentrations of up to one part of disinfectant and sanitizer to 256 parts of water.

In order to be registered for sale to the public, as required by the EPA, these products must be shown to completely kill specific pathogens. This kill ability (also known as log reduction) is based on accepted laboratory tests under controlled environmental conditions. The kill rate of each pathogen is measured in contact time, which can vary from a few seconds to 20 minutes or longer. Under laboratory testing conditions the pathogens are not contained in hard to remove biofilms such as are formed by dried blood, food grease, saliva and body fluids, which are typically found in actual use conditions in hospitals, nursing homes, restaurants, and many other sources of contamination. Biofilms are organic films or conglomerates under which pathogens can be located.

Cleaning compositions (which are different from disinfectant and sanitizing compositions) are also commercially important products that enjoy a wide utility in removing dirt and grime from surfaces, especially those characterized as "hard surfaces". Hard surfaces are those which are frequently encountered in lavatories and kitchens (food preparation facilities) and include, for example, lavatory fixtures such as toilets, shower stalls, bathtubs, bidets and sinks, as well as countertops, cabinet and appliance surfaces, walls and floors in, for example, grocery stores and offices.

There are many instances, in a variety of settings in which it may be desirable for a person to have clean hands. For example, in food handling or preparation, such as in grocery stores and restaurants, anyone handling food should (and in many cases may be required to) ensure that his or her hands are well cleaned before handling food. In a variety of medical and laboratory situations, it is necessary for personnel to clean their hands regularly, to prevent the transmission of disease and infection. Even in office settings, it may be desirable (if not necessary) for personnel to clean their hands regularly.

Although many facilities may be provided for cleaning or washing the hands, these may not be completely effective. At times, this requires that one seek out a washroom or the like, in order to wash or clean their hands. If washrooms are not readily available (even if water alone is not available) or are not properly maintained this can pose a problem vis-à-vis maintaining a requisite level of cleanliness.

Disinfecting and sanitizing cleaners are useful for preventing the spread of harmful bacteria. These cleaners are usually sprayed onto a surface and then wiped with a towel. Many known products must be sprayed several times to ensure that the disinfectant and/or sanitizer contacts the harmful bacteria or pathogens on the treated surface for a sufficient minimum contact time. However, many of these cleaners are toxic and as such must be rinsed from the treated surface prior to use.

These cleaners typically contain large amounts of alcohol or other solvents. Unfortunately, these solvents often result in rapid evaporation from the treated surface. As such, the necessary minimum contact time to ensure complete kill of the pathogens, or to fully penetrate the biofilm deposited on the surface being disinfected and sanitized may not be achieved. This latter problem can be especially insidious in that germs breed underneath the biofilm and in the biofilm, as well as on the surface of the biofilm. Thus, a cleaner that only works on the surface of a film is not able to thoroughly disinfect and sanitize. As such, when bacteria remain on the treated surface, they can produce an odor. In addition, such cleaners are ineffective even on biofilm surfaces because germs are not exposed to these cleaners for the required minimum contact time to assure complete pathogen kill. Moreover, many such "cleaners" do not in fact remove dead (or live) bacteria and organisms from an individual's hands.

Moreover, present methods of disinfecting and sanitizing surfaces typically require a number of steps to be effective. In fact, for currently available disinfectants and sanitizers to be effective, the surface must first be precleaned. For example, simply spraying a surface with a cleaner and then wiping does not fully disinfect and sanitize. Therefore, a disinfecting and sanitizing process may require first cleaning a surface, next spraying a liquid composition onto the surface and rubbing the sprayed liquid with a towel, then rinsing the cleaner off the surface, and finally drying the surface with still another towel. In addition, for the process to be truly effective, the surface must be kept wet by the cleaner, such as by re-spraying, to ensure that the disinfectant and sanitizer contact the bacteria for the requisite minimum time to achieve complete pathogen kill.

Still another drawback to known methods of disinfecting and sanitizing is that spray-type systems currently use low viscosity liquid cleaners that can run from the surface area to be treated. This can contaminate other surfaces that are not to be exposed to the cleaner and can further reduce the contact time on the surface that it is desired to clean. In addition, for current systems to actually penetrate a biofilm layer, an abrasive material must be used that can scratch the surface being disinfected and sanitized.

Still another disadvantage of known disinfecting and sanitizing systems is that many of these systems have limited disinfecting and sanitizing properties. For instance, the systems may kill only certain subclasses of bacteria. In other words, the systems may not have fungicidal, pseudomonacidal, tuberculocidal, bactericidal, and virucidal properties all combined in one system.

Thus, these conventional disinfectant and sanitizer solutions have not proven to be effective in actual use conditions (as compared to laboratory environments). They have been found to be ineffective due to: failure to completely remove the biofilm that contains the pathogens; insufficient contact time with the pathogen to complete a 100% kill; and the use of unsatisfactory cleaning towels that are necessary in current usage of disinfectant and sanitizer products. With respect to the towels, because the towels may not be saturated with disinfectant and sanitizer solutions to kill the pathogens which they absorb, they can actually spread infectious pathogens to other surfaces during the cleaning process by initially retaining absorbed pathogens into the towel and then releasing them onto other surfaces which are wiped.

Accordingly, there is a need for an article that effectively disinfects, sanitizes and deodorizes organic debris by breaking a biofilm surface and disinfecting and sanitizing underneath the film without the use of abrasive materials. Desirably, such an article provides one-step disinfecting and sanitizing in a safe, portable, convenient and easy to use product. More desirably, such a product has multiple disinfecting and sanitizing properties. There is also a need for a system of cleaning pathogens that achieves increased contact time with the pathogens and to provide a near complete (near 100 percent) kill. Most desirably, such a disinfecting and sanitizing article disinfects and sanitizes a surface and absorbs the pathogens without spreading unwanted pathogens to other surfaces.

BRIEF SUMMARY OF THE INVENTION

A disinfecting and sanitizing article is adapted for use on object to be disinfected and sanitized, such as skin and hands, as well as nonporous hard surfaces. The article is formed as a porous substrate formed from an absorbent fibrous matrix. The substrate is formed as an abrasive element.

A disinfecting and sanitizing agent is formulated as a liquid composition that is absorbed into the substrate. The composition is formulated from an organic solvent present in a concentration of about 10 percent to 40 percent by weight, a surfactant present in a concentration of about 0.5 percent to 20 percent by weight, one or more pathogen killing agents present in a concentration of about 0.255 percent to 10.5 percent by weight, an emollient present in a concentration of about 0.05 percent to 3.0 percent by weight, and water present in a concentration of about 50.0 percent to 89.9 percent by weight.

In a present article, the pathogen killing agents are dual chain quaternary (N-alkyldimethylethylbenzyl chloride, N-alkyldimethylethylbenzyl ammonium chloride), ortho phenyl phenol, paratertiary amyl phenol and/or parachlorometaxylenol. The organic solvent is preferably an alcohol and most preferably isopropyl alcohol and the surfactant is a nonionic surfactant. The article can includes a pH modifying agent, such as citric acid, present in a concentration of about 0.1 percent to about 2.0 percent by weight.

Application of the article provides an abrasive disinfecting and sanitizing action by a scrubbing action on the surface of the object to disinfected and sanitized. In one form, the substrate is a towel. Preferably, the towel is formed as an abrasive element. A plurality of the towels can be stored in an air-tight container. A disinfecting and sanitizing agent as well as a disinfecting and sanitizing kit are also disclosed.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
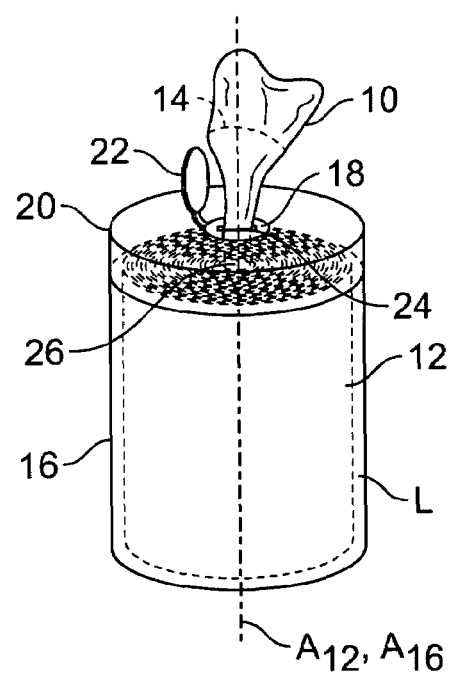
FIG. 1 is perspective view of an exemplary container for storing a plurality of disinfecting and sanitizing articles, formed as towels, for use on the skin and hands as well as hard surfaces, the container formed as a cylindrical container in which the towels are in a roll form, and from which the towels are withdrawn from the center of the roll through an opening in a lid of the container.
Figure 2:
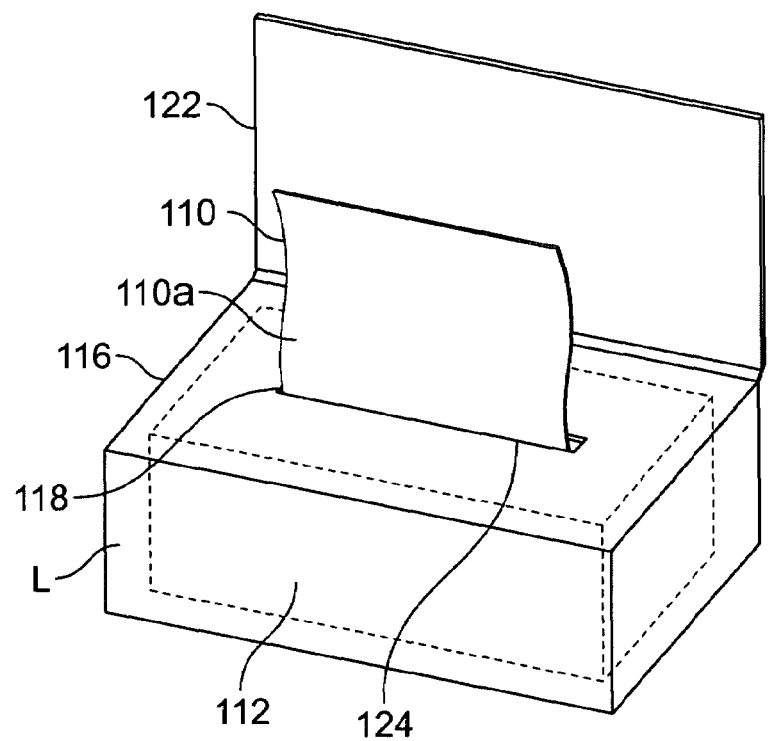
FIG. 2 is a top view of another exemplary container, formed in a rectangular shape, the towels being interfolded with one another and having a slot-like opening for withdrawing the towels.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

A disinfectant and sanitizer article includes a substrate and a pathogen killing disinfecting and sanitizing liquid composition incorporated in the substrate. The substrate is, for example, a towel. In one embodiment, the substrate is an abrasive material, preferably an abrasive cloth-like towel having at least one abrasive surface. The abrasive surface can be formed in several different ways from a variety of materials. For example, the towel can be formed as layered meltblown abrasive sheets, suitable as wet wipes. Such sheets typically exhibit liquid concentration stability over long periods of time such that stacks of these sheets maintain equal liquid concentration from the top to the bottom of the stack notwithstanding evaporation losses through the top of the stack. An example of such sheets is described in Win et al., U.S. Pat. No. 4,833,003.

The towel has two surfaces and the abrasive component can be permanently attached to or an integral part of one or both of the surfaces of the towel. Abrasive is intended to include an abrasive ingredient or component that has a surface texture that enables the towel to produce a mild scrubbing, scouring or abrading action to effectively break biofilms, such as dried blood, saliva, food grease, or other similar contaminants. In addition, the abrasive characteristics facilitate removing dried or embedded organic debris from a surface to be treated, while not harming that surface by scratching or the like.

The degree of abrasiveness can vary widely, depending primarily upon the abrasive component on the substrate and the degree of texture which is formed by such abrasive component. Typically, the abrasive surface is somewhat coarse and roughened as compared to a smooth surface of the towel. A preferred towel is adequately mildly abrasive to avoid scratching or otherwise harming the surface intended to be disinfected or sanitized by the towel, while having sufficient abrading qualities to effectively break biofilm layers on the treated surface. Although the abrasive properties are very mild in the sense of not cutting or scratching the surface being disinfected or sanitized, the texture is relatively high to remove dried or embedded organic debris from the object being disinfected and sanitized.

The abrasive component can be formed from a layer of fibers and/or globules bonded to the surface of a substrate, such as a layer of fibers or fiber bundles and minute, generally spherical masses having a wide range of acceptable diameters, namely from about 40 microns to about 200 microns. Due to the irregular nature of such fibers and globules it is recognized that the diameter is approximate and that the fibers and globules typically are not perfectly round. These fibers and globules can be formed from polymeric materials by, for example melt blowing, bonding, spinning and the like. Alternately, the abrasive can be formed from any number of known particulates that can function as an abrasive when bonded to a substrate.

To be effective, the abrasive component of this invention can account for a minimum of 10 percent and a maximum of 90 percent of the surface area of the abrasive side of the towel, with the other side of the towel having a smooth surface for wiping. It is anticipated that both sides of the towel can have abrasive components incorporated thereon, and that the percentage of abrasive component on each side can differ as desired for a particular application.

In addition to the abrasive characteristics, the towel should be capable of absorbing and retaining a predetermined amount of fluid, such as the liquid disinfectant and sanitizer emulsion formulation. In a preferred towel, liquid is absorbed in an amount sufficient to provide a uniformly moist towel. The absorbent character of the towel can be achieved by a system of voids or pores that absorb and retain the liquid, for example, by capillary action. The towel should also be capable of readily releasing the liquid during use. The specific void or pore volume of the structure of the towel regulates the amount of fluid that can be retained in the towel.

In one embodiment the towel is formed from a non-woven material having an affinity for absorbing the fluid. Such a towel is also able to absorb or otherwise retain organic debris that has been removed from the treated surface. Suitable substrates for forming the towel include non-woven materials, fibrous natural or manufactured materials, including regenerated and synthetic materials such as polypropylene, polyester nylon, rayon, cotton, wood pulp, cellulose, polyethylene, polyvinyl, viscose, polyurethane, and blends thereof.

The liquid disinfectant and sanitizer composition is capable of killing highly resistant pathogens such as *mycobacterium tuberculosis* (TB), *salmonella choleraesuis, staphylococcus aureaus, psedumonas aeroginosa,* and other like pathogens including viral, mold, and hepatitis. The composition has a viscosity sufficient for being easily absorbed into the pores or voids of the towel through capillary action. The composition of a preferred disinfectant and sanitizer includes pathogen killing agents, such as quaternary ammonium chloride, ortho phenyl phenol, paratertiary amyl phenol and parachlorometaxylenol (PCMX) in water, aloe vera gel, non-ionic surfactant(s), organic solvent(s), and a pH modifying agent.

Various exemplary compositions were formulated. These exemplary formulations, identified as Example 1, 1A and 1B and Examples 2, and 2A-2E. Example 1 is a general formulation providing the types of constituents, whereas Example 1A provides the various specific constituents and ranges of concentration for each of the specific constituents and Example 1B provides the specific constituents and concentrations.

EXAMPLE 1

| Ingredient | Acceptable range (Percent by weight) |
|---|---|
| Pathogen killing agent(s) | 0.255-10.0 |
| Organic solvent | 10.0-30.0 |
| Nonionic surfactant | 0.1-2.0 |
| pH modifier | 0.05-2.0 |
| Emollient | 0.05-3.0 |
| Water | 50.0-89.9 |

EXAMPLE 1A

| Ingredient | Acceptable range (Percent by weight) |
|---|---|
| Dual chain quaternary (N-alkyl dimethyl ethylbenzyl chloride or N-alkyldiemethyl ethylbenzyl ammonium chloride) | 0.25-2.0 |
| Ortho phenyl phenol | 0.0025-2.0 |
| Paratertiary amyl phenol | 0.0025-2.0 |
| Alcohol | 10.0-40.0 |
| Tergitol 15-S-5 | 0.5-2.0 |
| Citric acid | 0.1-2.0 |
| Emollient | 0.1-3.0 |
| Water | 50.0-89.9 |

EXAMPLE 1B

| Ingredient | Specific composition formulation (Percent by weight) |
|---|---|
| Dual chain quaternary (N-alkyldimethylethylbenzyl chloride or N-alkyldimethylethylbenzyl ammonium chloride) | 0.25 |
| Ortho phenyl phenol | 0.0125 |
| Paratertiary amyl phenol | 0.0025 |
| Isopropyl alcohol | 20.0 |
| Tergitol 15-S-5 | 0.5 |
| Citric acid | 0.05 |
| *Aloe vera* gel | 1.0 |
| Water | 78.74 |

The dual chain quaternary ammonium chloride, ortho phenyl phenol, and para tertiary phenol are the pathogen killing agents. Alternate ingredients can be used in the formulation to replace any of the dual chain quaternary ammonium chloride, ortho phenyl phenol, and the para tertiary amyl phenol. For example, and as provided below in Examples 2-2E, iodine and glutaraldehyde can be used as alternate pathogen killing agents. It is also anticipated that parachlorometaxylenol (PCMX) can be used as an alternate pathogen killing agent.

One suitable organic solvent is and alcohol, preferably isopropyl alcohol, which in addition to providing a vehicle for the pathogen killing agents, acts as a synergist for the agents to effect a more complete and faster kill. Alcohols work by denaturing the proteins of the microorganisms (pathogens). As an alternative to isopropyl alcohol, ethanol, methanol, glycol, and glycol ethers may also be used for the same purpose. It is understood that the organic solvent as defined in this formulation can also comprise various combinations of these solvents.

One suitable ionic surfactant is a mixture of linear secondary alcohols reacted with ethylene oxide. This surfactant is commercially available from the Dow Chemical Company of Midland, Mich. as Tergitol 15-S-5. Tergitol 15-S-5 is a non-ionic surfactant that permits emulsification and which ultimately serves as a vehicle for the complete composition. Other surfactants can also be used including non-ionic and anionic surfactants, which other surfactants and emulsifying agents are within the scope of the present invention.

One pH modifying agent (modifier) is citric acid which is used to control the pH in that the phenols have enhanced disinfecting and sanitizing properties in a slightly acidic medium. In addition, the citric acid functions to remove noxious odors. Those skilled in the art will recognize that other acids such as oxalic acid and the like can also be used to modify the pH of the composition.

The emollient aids the composition in achieving a slower dry time. This permits longer exposure of the germ killing ingredients to the pathogens to bring about a more effective kill. One suitable emollient is aloe vera gel. A similar effect can also be obtained by using oils, such as mineral oil and refined vegetable oils. An additional benefit is that when the article is used for disinfecting and sanitizing the skin (e.g., for, skin cleaning applications) the emollient, e.g., the aloe vera gel, mineral and/or vegetable oils, function as a skin conditioner in to minimize skin drying and chaffing that could otherwise occur due to the alcohol.

As set forth above, additional examples of disinfectant formulations using various of the above-listed ingredients and using alternate pathogen killing agents.

EXAMPLE 2

| Ingredient | Acceptable range (Percent by weight) |
|---|---|
| Dual quaternary ammonium chloride compounds (50 percent conc.) | 0.25-5.0 |
| Ortho phenyl phenol | 0.0025-2.0 |
| Paratertiary amyl phenol | 0.0025-2.0 |
| Alcohol | 5.0-40.0 |
| Tergitol 15-S-5 | 0.2-2.0 |
| Citric acid | 0.05-2.0 |
| Aloe vera gel | 0.1-1.0 |
| Water (deionized) | 38.4-89.4 |
| Glutaraldehyde | 0.10-2.5 |
| Iodine | 0.005-2.0 |

In the formulation of Example 2, the Dual quaternary ammonium chloride compounds are disinfectants. Preferred dual quaternary ammonium chloride compounds are n-alkyl (60 percent C14, 30 percent C16, 5 percent C12, 5 percent C18) dimethyl benzyl ammonium chloride and n-alkyl (68 percent C12, 32 percent CH) dimethyl ethyl benzyl ammonium chloride in an equal ratio.

Example 2 provides the various specific constituents and ranges of concentration for each of the specific constituents of the alternate formulation and Example 2A provides the specific constituents and concentrations in which glutaraldehyde is used and Example 2B provides the specific constituents and concentrations in which iodine is used.

EXAMPLE 2A

| Ingredient | Specific composition formulation (Percent by weight) |
|---|---|
| Dual quaternary ammonium chloride compounds (50 percent conc.) | 0.50 |
| Ortho phenyl phenol | 0.70 |
| Paratertiary amyl phenol | 0.70 |
| Alcohol (isopropyl or ethyl) | 40.0 |
| Tergitol 15-S-5 | 0.60 |
| Citric acid | 0.05 |
| Aloe vera gel | 1.0 |
| Water (deionized) | 56.65 |
| Glutaraldehyde | 0.25 |

EXAMPLE 2B

| Ingredient | Specific composition formulation (Percent by weight) |
|---|---|
| Dual quaternary ammonium chloride compounds (50 percent conc.) | 0.50 |
| Ortho phenyl phenol | 0.80 |
| Paratertiary amyl phenol | 0.80 |
| Alcohol (isopropyl or ethyl) | 40.0 |
| Tergitol 15-S-5 | 0.50 |
| Citric acid | 0.05 |
| Aloe vera gel | 1.0 |
| Water (deionized) | 56.70 |
| Iodine | 0.20 |

In the following Example 2C, the formulation excludes glutaraldehyde and iodine in favor of a higher concentration of the dual quaternary ammonium chloride compounds (50 percent conc.).

EXAMPLE 2C

| Ingredient | Specific composition formulation (Percent by weight) |
|---|---|
| Dual quaternary ammonium chloride compounds (50 percent conc.) | 2.0 |
| Ortho phenyl phenol | 1.0 |
| Paratertiary amyl phenol | 1.0 |
| Methanol | 40.0 |
| Tergitol 15-S-5 | 1.50 |
| Citric acid | 0.05 |
| Aloe vera gel | 1.0 |
| Water (deionized) | 53.80 |

In Example 2D, below, the formulation includes both glutaraldehyde and iodine and substitutes glycol for alcohol.

EXAMPLE 2D

| Ingredient | Specific composition formulation (Percent by weight) |
| --- | --- |
| Dual quaternary ammonium chloride compounds (50 percent conc.) | 0.50 |
| Ortho phenyl phenol | 0.5 |
| Paratertiary amyl phenol | 0.5 |
| Alcohol (isopropyl or ethyl) | 35.0 |
| Tergitol 15-S-5 | 1.0 |
| Citric acid | 0.1 |
| *Aloe vera* gel | 1.0 |
| Water (deionized) | 55.8 |
| Glutaraldehyde | 2.5 |
| Iodine | 2.0 |

Example 2E provides the specific constituents and concentrations in which glutaraldehyde and iodine are both used.

EXAMPLE 2E

| Ingredient | Specific composition formulation (Percent by weight) |
| --- | --- |
| Dual quaternary ammonium chloride compounds (50 percent conc.) | 0.50 |
| Ortho phenyl phenol | 0.5 |
| Paratertiary amyl phenol | 0.5 |
| Alcohol (isopropyl or ethyl) | 20.0 |
| Tergitol 15-S-5 | 0.50 |
| Citric acid | 0.20 |
| *Aloe vera* gel | 1.0 |
| Water (deionized) | 77.05 |
| Glutaraldehyde | 0.25 |
| Iodine | 0.20 |

Referring to FIG. 1, in preparing a disinfecting and sanitizing article 10, a plurality of towels are provided, preferably in a continuous, perforated roll 12 of towels 10. In a preferred embodiment, the towels 10 are abrasive. The lines of perforation 14 provide lines of weakness by which the individual towels 10 can be easily separated. In a roll 12 form, the towels 10 are inserted on-end into a container 16. In a preferred form, the towel roll 12 is inserted into a resealable, preferably cylindrical container 16, with the axis $A_{16}$ of the cylinder 16 being aligned with an axis $A_{12}$ of the towel roll 12. In an alternate embodiment, a stack 112 of individual towels 110 (rather than the continuous roll of towels) can be introduced into a container 116 with, for example, a slot 118, through which the towels 110 can be retrieved from the container 116. The individual towels 110 can be interfolded so that as one towel 110 is pulled from the container 116, a first portion of a next towel 110a is also pulled through the slot 118.

The liquid disinfectant and sanitizer composition L can be added to the container 16, 116 by pouring the composition over the towels 10, 110, thereby saturating the towels 10, 110 in the container 16, 116. A combination of the viscosity of the composition and the capillary action associated with the void volume of the towels, as discussed above, causes the fluid to be distributed evenly throughout the towels. Alternately, the towels can be saturated by pre-towel saturation. This can be accomplished by post unwind and pre-perforation of a continuous roll of towels. This fully saturated roll 12 or stack 112 is then inserted into a finished goods container 16, 116.

The container 16 for holding the towels 10 (in roll form 12) includes an essentially airtight lid 20 on the top portion of the container 16 body. The lid 20 can be sealed and can include, for example, a hinged cap 22 with an opening 18 positioned under the cap 22. The opening 18 allows for the passage of towels 10 from the interior of the sealed container 16 via the opening 18. The individual towels 10 can be removed by pulling the towel 10 and tearing the towel 10 off of the roll 12 at the perforation line 14 between the individual towels 10. The opening 18 is appropriately sized to allow for removing each individual towel 10 removed from the container 16 and to provide an edge against which (or at which) the towel can be separated from the other towels on the roll 12. That is, the edge of the opening 18 helps to "tear" the towel 10 (e.g., singulate the towel 10) at the perforation line 14 so that one towel at a time can be dispensed from the container 16. In the alternate embodiment 116, the slot edge 124 serves to separate the towel 110 (e.g., singulate the towel 110) from a next towel in stack 116. The liquid L and the lid 122 maintains the towels 110 moist (prevents evaporation of the liquid emulsion). The entirety of the towels 10, 110 in the liquid L in their containers 16, 116 constitutes a disinfecting and sanitizing kit.

It is expected that each towel will contain an amount of the liquid disinfectant and sanitizer composition sufficient to disinfect and sanitize the treated surface and thoroughly remove organic debris. As the towel is rubbed on the surface, it releases the liquid disinfectant and sanitizer and allows the liquid to have an extended contact time with the bacteria and other pathogens on the treated surface. This arrangement also provides for continuous disinfecting and sanitizing without the need for additional applications of the liquid. Advantageously, the abrasive character of the towel works in conjunction with the liquid disinfectant and sanitizer to break the biofilm without leaving any abrasive residue on the treated surface. This prevents residue that would otherwise require rinsing the surface with water after the disinfecting and sanitizing process to thoroughly remove the abrasive residue.

In addition, the pathogens that are absorbed into the towel during the disinfecting and sanitizing process are killed by the composition that is impregnated into the towel. This further prevents the pathogens from being transferred to other surfaces. Moreover, the nature of the present disinfecting and sanitizing article facilitates cleaning without leaving a toxic layer that otherwise would need to be rinsed and/or wiped with additional towels or other tools.

A presently contemplated towel is formed from a nonwoven polypropylene that is can absorb organic debris so as to achieve a thoroughly disinfected surface. Alternately, the towel is formed from a bicomponent fiber matrix that is able to absorb organic debris to achieve a thoroughly disinfected surface. The present disinfecting and sanitizing article is useful in disinfecting and sanitizing the hands and skin, as well as non-porous surfaces in hospitals and other health-related facilities, health clubs, schools, medical offices, veterinary facilities, hotels, restaurants, public facilities, and day care facilities, and grocery stores and general office facilities.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An abrasive disinfecting and sanitizing article, consisting essentially of, in combination to obtain a slower drying time of its liquid composition:
    a towel substrate formed from an absorbent fibrous matrix, the substrate having two opposed surfaces, at least one of the opposed surfaces having an abrasive component permanently attached thereto or an integral part thereof; and,
    a disinfecting and sanitizing agent formed as a liquid composition in the substrate, the agent formulated from:
    an organic solvent being an alcohol present in a concentration of about 10 percent to 40 percent by weight;
    a nonionic surfactant system present in a concentration of about 0.5 percent to 20 percent by weight wherein the nonionic surfactant comprises a mixture of linear secondary alcohols reacted with ethylene oxide;
    one or more pathogen killing agents present in a concentration of about 0.255 percent to 10.5 percent by weight, wherein the one or more pathogen killing agents are dual chain quaternary (N-alkyldimethylethylbenzyl chloride, N-alkyldimethylethylbenzyl ammonium chloride), ortho phenyl phenol, paratertiary amyl phenol and parachlorometaxylenol;
    an emollient present in a concentration of about 0.05 percent to 3.0 percent by weight, the emollient being an aloe vera gel providing a slower drying time of the liquid composition;
    a pH modifying agent present in a concentration of about 0.05 percent to about 2.0 percent by weight; and
    water present in a concentration of about 50.0 percent to 89.9 percent by weight,
    wherein the abrasive component accounts for about 10 percent to 90 percent of a surface area of the at least one of the opposed surfaces,
    and wherein application of the substrate with the agent absorbed therein on object to be disinfected and sanitized provides an abrasive disinfecting and sanitizing action by a scrubbing action on the object.

2. A disinfecting and sanitizing kit, consisting essentially of, in combination, to obtain a slower drying time of a liquid composition:
    an air-tight container configured to retain a liquid, and retard evaporation of the liquid, the container having a lid that is closable to substantially prevent evaporation of the liquid;
    an abrasive porous substrate formed from an absorbent fibrous matrix, the substrate being disposed in the container and the substrate being formed as a plurality of singulatable towels, each towel having two opposed surfaces, at least one of the opposed surfaces having an abrasive component permanently attached thereto or an integral part thereof;
    a liquid composition disinfecting and sanitizing agent the liquid composition being absorbed in the substrate to form a disinfecting and sanitizing article, the liquid composition comprising:
    an organic solvent being an alcohol present in a concentration of about 10 percent to 40 percent by weight,
    a nonionic surfactant system present in a concentration of about 0.5 percent to 20 percent by weight, wherein the nonionic surfactant comprises a mixture of linear secondary alcohols reacted with ethylene oxide;
    one or more pathogen killing agents present in a concentration of about 0.255 percent to 10.5 percent by weight, wherein the one or more pathogen killing agents are dual chain quaternary (N-alkyldimethylethylbenzyl chloride, N-alkyldimethylethylbenzyl ammonium chloride), ortho phenyl phenol, paratertiary amyl phenol and parachlorometaxylenol;
    an emollient present in a concentration of about 0.05 percent to 3.0 percent by weight, the emollient being an aloe vera gel and providing a slower drying time for the liquid composition,
    a pH modifying agent present in a concentration of about 0.05 percent to about 2.0 percent by weight, and
    water present in a concentration of about 50.0 percent to 89.9 percent by weight,
    wherein the abrasive component accounts for about 10 percent to 90 percent of a surface area of the at least one of the opposed surfaces, and
    wherein the article is adapted for use on an object to be disinfected and sanitized, including skin and hands and nonporous hard surfaces, and
    wherein application of the article provides an abrasive disinfecting and sanitizing action by a scrubbing action on the surface of the object, and
    wherein the article is stored in the container to maintain the article is a wetted condition.

3. The disinfecting and sanitizing kit in accordance with claim 2 wherein the towels are formed as a roll of towels having a series of perforations therein to singulate the towels from one another.

4. The disinfecting and sanitizing kit in accordance with claim 2 wherein the towels are formed as a series of interfolded towels.

5. The disinfecting and sanitizing kit in accordance with claim 2 wherein the container has an opening therein through which singulatable towels are withdrawn from the container.

* * * * *